United States Patent [19]

Holzer

[11] 4,167,622

[45] Sep. 11, 1979

[54] PROCESS FOR PREPARING HYDROXYETHYL STARCH SUITABLE AS A PLASMA EXPANDER

[75] Inventor: Karl Holzer, Linz, Austria

[73] Assignee: Laevosan-Gesellschaft mbH & Co KG, Linz, Austria

[21] Appl. No.: 894,447

[22] Filed: Apr. 7, 1978

[30] Foreign Application Priority Data

Apr. 8, 1977 [AT] Austria ................................ 2489/77

[51] Int. Cl.$^2$ ............................................. C08B 33/04
[52] U.S. Cl. ..................................... 536/111; 424/180
[58] Field of Search ......................................... 536/111

[56] References Cited

U.S. PATENT DOCUMENTS

| | | | |
|---|---|---|---|
| 3,414,530 | 12/1968 | Zilkha et al. | 536/111 |
| 3,523,938 | 8/1970 | Hershenson et al. | 536/111 |
| 3,937,821 | 2/1976 | Irikura et al. | 536/111 |

*Primary Examiner*—Melvyn I. Marquis
*Attorney, Agent, or Firm*—Sughrue, Rothwell, Mion, Zinn and Macpeak

[57] ABSTRACT

A process for preparing hydroxyethyl starch suitable as a plasma extender by alkaline hydroxyethylation and neutralization wherein the hydroxyethyl starch is extracted with a solvent such as dimethylformamide to remove the salts formed on neutralization.

1 Claim, No Drawings

PROCESS FOR PREPARING HYDROXYETHYL STARCH SUITABLE AS A PLASMA EXPANDER

BACKGROUND OF THE INVENTION

1. Field of the Invention

The present invention relates to a process for the preparation of hydroxyethyl starch for use as a plasma expander.

2. Discussion of the Prior Art

W. Ziese, Z. Physiol. Chem. 229, 213 (1934); 235, 235 (1935), synthesized already 1934 hydroxyethyl starches (HES) and tested them as substrates for amylases of different origin. Husemann and Resz, Journal of Polym. Science 19, 389 (1959), synthesized HES as model substance for amylose so as to study fermentative degradation and to discover possible degradation in different reactions. Processes for preparing HES for industrial purposes have been known even longer and have been disclosed in many patent specifications. The use of HES for medical purposes as a plasma substitute in animals was described for the first time by Wiedersheim, Arch. Int. Pharmacodyn. Therap. 111, 353–61 (1957).

Wiedersheim prepared HES using the known process of hydroxyethylation of starch in alkaline-aqueous medium by means of ethylene oxide. However, he used corn starch hydrolytically degraded to lower molecular weights as the hydroxyethylation substrate so as to obtain HES suitable as a plasma substitute. In succession, numerous works and patents were published concerning the preparation of HES for human therapy.

As already mentioned, up to now, the hydroxyethyl starch which has been used in recent time as a plasma expander has been prepared by alkaline hydroxyethylation of starch. The reaction mixture which is obtained thereby is strongly alkaline and must be neutralized before it can be further worked up. The neutralization step produces a relatively large amount of salt, typically sodium chloride, in the reaction mixture. Dialysis methods have been proposed for removing the salt. However, such methods are extremely expensive with respect to time, apparatus and energy, and involve, furthermore, the danger of contaminating the reaction mixture. Therefore, many attempts have been made to replace this complicated process by a simpler working up process. Thus, it has been proposed, for example, to carry out the neutralization of the reaction solution with cation exchang resins. It is true that such a process is simpler with respect to the apparatus; however, that process does not prevent the danger of biological contamination (infection) of the preparation due to the great surface area of the exchange resin particles being readily populated with bacteria and fungi.

Summarizing, according to the previously known processes, it is only with extreme difficulty that hydroxyethyl starch can be prepared having the necessary purity and sterility to be used as a plasma substitute.

SUMMARY OF THE INVENTION

I have discovered a relatively simple and surprisingly effective process by which the problems mentioned above can be avoided and by which hydroxyethyl starch may be obtained in pyrogen-free form having the necessary purity to be used as a plasma expander.

Therefore, the present invention relates to a process for the preparation of hydroxyethyl starch suitable as a plasma expander by alkaline hydroxyethylation of starch and subsequent neutralization of the reaction mixture, which is characterized in that the hydroxyethyl starch which is formed after neutralization is extracted from the reaction mixture by a solvent, such as dimethylformamide, in which the salts formed by the neutralization are only slightly soluble or insoluble altogether.

DESCRIPTION OF THE INVENTION

In more detail, the process of the invention is carried out as follows.

After the hydroxyethylation of the starch, which is conveniently carried out as described by Husemann and Resz (incorporated herein by reference), the neutralized reaction solution is filtered under pressure with activated carbon, evaporated in vacuo, and the thick syrup is dehydrated by drying in vacuo. The dried product is dissolved in an extraction solvent, the main portion of the sodium chloride derived from the neutralization being undissolved and thereby separated. After filtration, the filtrate which is obtained consists substantially of a solution of hydroxyethyl starch in the solvent and contains, in addition to a small amount of residual sodium chloride, ethyleneglycols which are formed as by-products of the hydroxy ethylation.

Advantageously, the crude hydroxyethyl starch is precipitated from the filtrate by stirring with a precipitating agent in which the hydroxyethyl starch is slightly soluble to insoluble. It is convenient to use acetone as a precipitating agent. For purification, a solution of the HES product in water is treated in activated carbon and re-precipitated in acetone. The pure product is free of pyrogen and contains little sodium chloride, as can be determined potentiometrically. In working up to obtain a 6% isotonic solution of hydroxyethyl starch plasma expander the calculated missind amount of sodium chloride is added.

Preferably, dimethylformamide is used as an extraction solvent. Also dimethylsulfoxide may be used. However, other solvents can be determined by those of ordinary skill in the art without undue experimentation, the requirements of the solvent being that it extract the hydroxyethyl starch substantially without dissolving the contaminating salt neutralization by-products.

As pointed out above, the HES is preferably removed from the extraction solvent by precipitation. Acetone or isopropanol is generally used for this purpose, but other precipitating agents can easily be determined by those of ordinary skill in the art, the object being to force HES out of solution by the addition of the precipitating agent in accordance with familiar practice.

In the practice, it has been found that the content of residual sodium chloride in the HES product of this invention is below that of a solution of hydroxyethyl starch plasma expander containing 0.9% of sodium chloride. Accordingly, in making many isotonic solutions of HES plasma expander it is necessary to supplement the amount of sodium chloride up to the required value.

The hydroxyethyl starch obtained by the above process has a molar ratio of 2-O-hydroxyethylanhydroglucose to 6-O-hydroxyethylanhydroglucose of about 1 due to the molar ratio of alkali to starch of 4:1 used in the hydroxyethylation; therefore, it is cleaved relatively easily by endogenous amylases and separated within an acceptable period from the organism.

The following example explains the present invention without limiting it thereto.

EXAMPLE 1

243 g of wax corn starch partially degraded by acid hydrolysis having $\eta = 2.35$ cP (c=6, water, 37° C.) was dissolved in a solution of 240 g of sodium hydroxide in 6 l of water with stirring under fumigation with nitrogen at room temperature. 317 g of ethylene oxide in gaseous form was introduced within 2-3 hours into the yellow alkaline solution of the degraded starch and cooled with water and with further fumigation with nitrogen. After standing for several hours under nitrogen, the solution was neutralized with diluted hydrochloric acid (from 480 ml of concentrated hydrochloric acid, d=1.19, 37%, and 3 l of water) while cooling with water (pH about 6). After stirring with 15 g of activated carbon (Norite SX plus), it is filtered under pressure, and the filtrate is evaporated in vacuo at a temperature of 60° C. For drying purposes, it was heated to 60° C. in an oil pump vacuum for a period of 15-20 hours. The dried product was rotated in 900 ml of dimethylformamide at a temperature of 80° C. until a homogeneous turbid solution was obtained. After cooling to room temperature, the solution was drawn off by suction. The sodium chloride remained on the filter and was washed out with dimethylformamide. The filtrate was stirred with about 10 l of acetone, and the crude HES precipitated in the form of yellow granules which were drawn off by suction, washed out with acetone and dried in vacuo at a temperature of 60° C. to obtain a glassy-bubbly mass. Yield 352 g.

For purification, the mass was dissolved in 2 l of water with slight heating, filtered with 22 g of active carbon, the filtrate is concentrated in vacuo at a temperature of 60° C. to obtain 900 ml and stirred with 9 l of acetone. The precipitated resinous mass was kneaded twice with fresh acetone and dried in vacuo at a temperature of 60° C. Yield 272 g.

For further purification, the yields of five such batches, totaling about 1350 g, were dissolved in 9.5 l of water with stirring, after stirring with 64 g of activated carbon and filtered under pressure. The filtrate was stirred with the same amount of activated carbon and again filtered under pressure. Subsequently, it was concentrated in vacuo at a temperature of 60° C. to about 4 l and stirred with 20 l of acetone. The white resin was kneaded thrice with fresh acetone and then dried in vacuo at a temperature of 60° C. Yield 1173 g of a foamy white solid substance having $\eta = 2.95$ cP (c=6, water, 37° C.); degree of substitution=0.71; content of sodium chloride=5.2%, pyrogen test: negative.

Having described my invention above, it will be apparent to the artisan that numerous variations thereof are possible without departing from the meaning and scope of the following claims.

What is claimed is:

1. In a process for preparing hydroxyethyl starch suitable as a plasma expander by alkaline hydroxyethylation of starch, neutralization of the resulting reaction mixture, extraction of the formed hydroxyethyl starch from the neutralized reaction mixture with a solvent and precipitation of the hydroxyethyl starch from the solution resulting from the extraction, the improvement which comprises the use of dimethylformamide as extracting solvent.

* * * * *